United States Patent
Maguire-Boyle et al.

(10) Patent No.: US 10,591,634 B2
(45) Date of Patent: *Mar. 17, 2020

(54) SPECTRALLY PROGRAMMABLE MEMRISTOR-BASED OPTICAL COMPUTING

(71) Applicant: Halliburton Energy Services, Inc., Houston, TX (US)

(72) Inventors: Samuel James Maguire-Boyle, Houston, TX (US); Aditya B. Nayak, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 52 days.

This patent is subject to a terminal disclaimer.

(21) Appl. No.: 15/552,689

(22) PCT Filed: Apr. 23, 2015

(86) PCT No.: PCT/US2015/027320
§ 371 (c)(1),
(2) Date: Aug. 22, 2017

(87) PCT Pub. No.: WO2016/171700
PCT Pub. Date: Oct. 27, 2016

(65) Prior Publication Data
US 2018/0031729 A1 Feb. 1, 2018

(51) Int. Cl.
*G01V 9/00* (2006.01)
*G02F 1/03* (2006.01)
(Continued)

(52) U.S. Cl.
CPC ............... *G01V 9/00* (2013.01); *G01N 21/85* (2013.01); *G02B 6/122* (2013.01); *G02F 1/011* (2013.01);
(Continued)

(58) Field of Classification Search
CPC .......... G01V 9/00; G01N 21/85; G01N 21/59; G01N 21/31; G02F 1/011; G02F 1/0121;
(Continued)

(56) References Cited

U.S. PATENT DOCUMENTS 3,488,636 A  1/1970 Dyck
3,801,966 A  4/1974 Terao
(Continued)

FOREIGN PATENT DOCUMENTS

WO  WO 2010/082929 A1  7/2010

OTHER PUBLICATIONS

Emboras et al., "Nanoscale Plasmonic Memristor With Optical Readout Functionality," *Nano Letters*, Issue No. 13,Volumen No. 12, Nov. 22, 2013, pp. 6151-6155.
(Continued)

*Primary Examiner* — Helen C Kwok (57) ABSTRACT

A memristor element is used to create a spectrally programmable optical computing device for use in, for example, a downhole environment. An electromagnetic field is applied across the memristor element in order to alter its spectral properties. In turn, the spectral properties of sample-interacted light optically interacting with the memristor element are also altered. This alteration in spectral properties allows the memristor to be "programmed" to achieve a variety of transmission/reflection/absorption functions.

25 Claims, 4 Drawing Sheets (51) Int. Cl.
*G02F 1/01* (2006.01)
*G11C 13/00* (2006.01)
*G11C 13/04* (2006.01)
*G02F 1/09* (2006.01)
*G01N 21/85* (2006.01)
*G02B 6/122* (2006.01)

(52) U.S. Cl.
CPC .............. *G02F 1/0121* (2013.01); *G02F 1/03* (2013.01); *G02F 1/091* (2013.01); *G11C 13/0007* (2013.01); *G11C 13/0069* (2013.01); *G11C 13/04* (2013.01); *G02F 2202/10* (2013.01)

(58) Field of Classification Search
CPC .......... G02F 1/03; G02F 1/091; G01S 7/4811; G01S 7/491; G01S 7/497; G01S 7/4915
See application file for complete search history.

(56) References Cited

U.S. PATENT DOCUMENTS

| | | | |
|---|---|---|---|
| 5,987,343 A * | 11/1999 | Kinast | A61B 5/14551 600/323 |
| 7,580,596 B1 | 8/2009 | Meijer et al. | |
| 7,596,016 B2 | 9/2009 | Johnson | |
| 7,768,815 B2 | 8/2010 | Chen et al. | |
| 7,991,253 B2 | 8/2011 | Bratkovski et al. | |
| 8,081,129 B1 * | 12/2011 | Santori | H01Q 1/2225 343/745 |
| 8,149,485 B2 | 4/2012 | Li et al. | |
| 8,477,408 B2 | 7/2013 | Li | |
| 8,542,518 B2 | 9/2013 | Bratkovski et al. | |
| 8,659,510 B2 | 2/2014 | Fattal et al. | |
| 10,302,973 B2 * | 5/2019 | Maguire-Boyle | G02F 1/011 |
| 2006/0092006 A1 * | 5/2006 | Grando | B60R 21/0136 340/438 |
| 2009/0109516 A1 * | 4/2009 | Wang | G03H 1/02 359/290 |
| 2009/0265287 A1 | 10/2009 | Haas | |
| 2010/0026984 A1 * | 2/2010 | Lewis | G01S 7/4811 356/5.01 |
| 2010/0027014 A1 * | 2/2010 | Hart | A61C 5/90 356/436 |
| 2010/0226163 A1 * | 9/2010 | Savransky | G11C 13/0004 365/148 |
| 2010/0265552 A1 * | 10/2010 | Wang | B82Y 20/00 359/9 |
| 2010/0277789 A1 * | 11/2010 | Wu | G02F 1/01 359/276 |
| 2010/0278474 A1 * | 11/2010 | Beausoleil | H01S 5/1032 385/2 |
| 2011/0169815 A1 * | 7/2011 | Fattal | G02F 1/292 345/212 |
| 2011/0227032 A1 * | 9/2011 | Xia | B82Y 10/00 257/5 |
| 2011/0242873 A1 * | 10/2011 | Bratkovski | G11C 13/0007 365/112 |
| 2011/0273755 A1 | 11/2011 | Wang et al. | |
| 2012/0154880 A1 * | 6/2012 | Wu | G02F 1/0102 359/9 |
| 2012/0250017 A1 * | 10/2012 | Morys | G01N 21/31 356/335 |
| 2012/0281980 A1 | 11/2012 | Cho et al. | |
| 2013/0050409 A1 * | 2/2013 | Li | G03H 1/02 348/41 |
| 2013/0076950 A1 | 3/2013 | Eshraghian et al. | |
| 2013/0201544 A1 * | 8/2013 | Lezec | G02F 1/1533 359/265 |
| 2013/0286398 A1 * | 10/2013 | Freese | G01N 21/59 356/432 |
| 2014/0027702 A1 | 1/2014 | Lu et al. | |
| 2018/0113330 A1 * | 4/2018 | Maguire-Boyle | G02F 1/011 |

OTHER PUBLICATIONS

He, et al., "Tunable Electroluminescence in Planar Graphene/Sio2 Memristors," *Advanced Materials*, vol. 25, No. 39, Oct. 1, 2013, pp. 5593-5598.
International Search Report and The Written Opinion of the International Search Authority, or the Declaration, dated Dec. 29, 2015, PCT/US2015/027320, 18 pages, ISA/KR.
Yakopcic et al., "Memristor-Based Unit Cell for a Detector Readout Circuit," In *SPIE Optical Engineering+Applications*, International Society for Optics and Photonics, Sep. 8, 2011, pp. 81651F-81651F.
Yilmaz et al., "Image Processing by a Programmable Grid Comprising Quantum Dots and Memristors," IEEE Transactions on Nanotechnology, vol. 12, No. 6, Nov. 2013, pp. 879-887.

* cited by examiner

SPECTRALLY PROGRAMMABLE MEMRISTOR-BASED OPTICAL COMPUTING

PRIORITY

The present application is a U.S. National Stage patent application of International Patent Application No. PCT/US2015/027320, filed on Apr. 23, 2015, the benefit of which is claimed and the disclosure of which is incorporated herein by reference in its entirety.

FIELD OF THE DISCLOSURE

Embodiments of present disclosure generally relates to optical sensors and, more particularly, to an optical computing device which uses spectrally programmable memristors.

BACKGROUND

In recent years, optical computing techniques have been developed for applications in the oil and gas industry in the form of optical sensors in downhole or surface equipment to evaluate a variety of fluid properties. In general, an optical computing device is a device configured to receive an input of electromagnetic radiation from a sample and produce an output of electromagnetic radiation from a processing element, also referred to as an optical element, wherein the output reflects the measured intensity of the electromagnetic radiation. The optical element may be, for example, an Integrated Computational Element, or ICE. One type of an ICE is an optical thin film optical interference device, also known as a multivariate optical element ("MOE").

Fundamentally, optical computing devices utilize the optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE and one or more detectors, is capable of extracting the information of one or multiple characteristics/analytes within a substance and converting that information into a detectable output signal reflecting the overall properties of a sample. Such characteristics may include, for example, the presence of certain elements, compositions, fluid phases, etc. existing within the substance.

Historically, the thin-film MOEs have been designed and fabricated using alternating layers of high-index and low-index materials deposited on a substrate. Once the materials have been deposited on the substrate, however, the transmission/reflection/absorption functions of the MOE are fixed due to the fundamental nature of the design and fabrication process. Therefore, once the film stack has been deposited, its spectral properties cannot be changed.

DESCRIPTION OF ILLUSTRATIVE EMBODIMENTS

Illustrative embodiments and related methods of the present disclosure are described below as they might be employed in an optical computing device comprising spectrally alterable memristors. In the interest of clarity, not all features of an actual implementation or method are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methods of the disclosure will become apparent from consideration of the following description and drawings.

As described herein, the present disclosure is directed to an optical computing device which uses a memristor element to create a spectrally programmable optical device. A memristor, or "memory resistor," is a non-linear electrical component in which its resistance is related to the electrical voltage applied across it. In a generalized embodiment of the present disclosure, electromagnetic radiation optically interacts with a sample to produce sample-interacted light, which is then directed to a memristor element made of spectrally alterable material. An electromagnetic field is applied across the memristor element in order to alter its spectral properties. In turn, the spectral properties of the sample-interacted light optically interacting with the memristor element are also altered, to thereby produce optically-interacted light. This alteration in spectral properties allows the memristor to be "programmed" to achieve a variety of transmission/reflection/absorption functions. The optically-interacted light is then detected by one or more detectors, whereby sample characteristics are determined. As a result, the memristor-based optical computing devices of the present disclosure may be utilized in a variety of applications, including, for example, multi-functional downhole optical sensors.

As previously mentioned, thin-film optical elements have been designed and fabricated using alternating layers of high-index and low-index materials deposited on a substrate. The fundamental equations governing the transmission, reflection and absorption functions of thin-film optical elements are the Fresnel equations, derived from Maxwell's equations. The choice of materials is based on the application and the range of wavelengths of interest. As an example, for an infrared application, one might choose a-Si (Amorphous Silicon) as the high index material, $SiO_2$ (Silicon-dioxide) as the low index material and glass as the substrate. The fabrication methods typically include PVD (Physical Vapor Deposition such as, for example, electron-beam vacuum deposition, RF magnetron sputtering, etc.), CVD (Chemical Vapor Deposition, such as MOCVD, PECVD etc.), ALD (Atomic Layer Deposition), etc.

As also mentioned, illustrative embodiments of the present disclosure utilize spectrally programmable memristor elements. The memristor elements are non-linear electrical components relating electrical charge and magnetic flux. The fundamental equation that governs the linkage of electrical charge (q) and magnetic flux ($\Phi$) is shown as:

$$d\Phi = Mdq \qquad \text{Eq.(1),}$$

also known as the circuit theory equation for a memristor. In Equation 1, $\Phi$ is the magnetic flux, M is the resistance of the memristor, and q is the charge. Accordingly, this type of device shows relationship between the resistance and electrical voltage applied across the memristor element.

Figure 1:
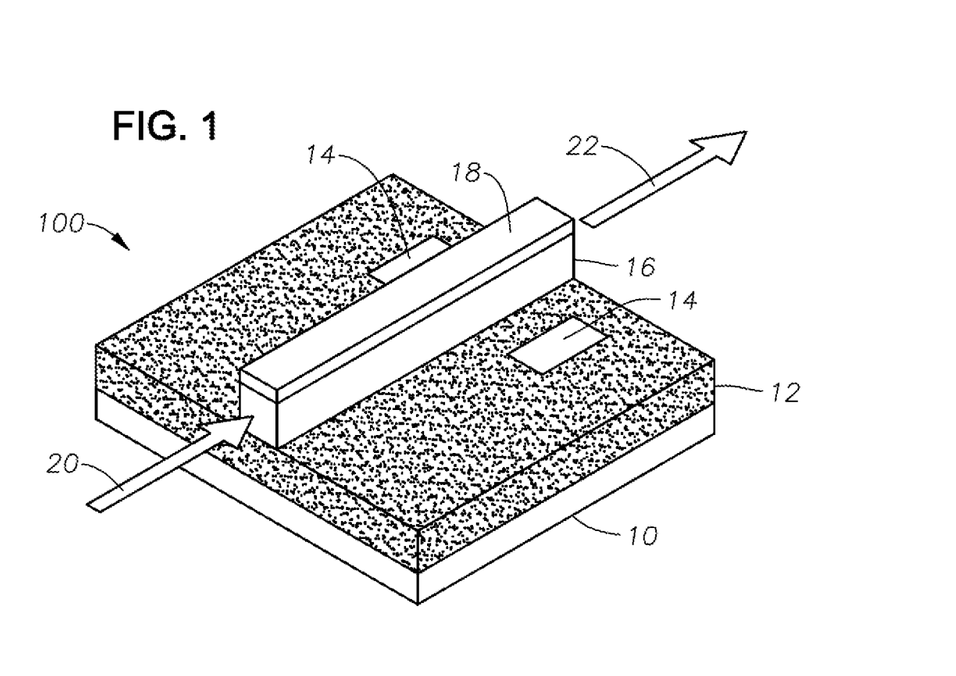
FIG. 1 illustrates a memristor element which may be utilized in a spectrally programmable optical thin-film device in transmission mode, according to certain illustrative embodiments of the present disclosure.

FIG. 1 illustrates a memristor element which may be utilized in a spectrally programmable optical computing device in transmission mode, according to certain illustrative embodiments of the present disclosure. In a generalized embodiment, the fundamental component of the optical computing device is a memristor element 100, as shown in FIG. 1. In this example, memristor element 100 is a single memristor pixel as shown; however, in other embodiments, the memristor element may be comprised of a plurality of memristor pixels. "Memristor pixel" refers to a single memristor. Nevertheless, memristor element 100 consists of a metal/semiconductor interface comprised of an insulator/dielectric layer 10, pure semiconductor layer 12 having metal contacts 14 positioned thereon, semiconductor layer 16 having defects therein, and a metal layer 18. The "defects" in semiconductor layer 16 refers to non-pure semiconductors with defects in the crystal lattice which may be manufactured in a variety of ways. In other embodiments however, the same functionality can be achieved by a dielectric/semiconductor interface or a metal/metal-oxide interface.

In certain embodiments, the metal/semiconductor interface can be fabricated using standard processing techniques, such as, for example, PVD, CVD or ALD. Semiconductor layer 16 is deposited with a high level of defects present in the crystal lattice of the material such that diffusion of metal ions can occur when electromagnetic radiation (e.g., an electrical voltage) is applied across the device via metal layer 18 and contacts 14. Selection of the metal, semiconductor, defect level, etc., will depend on the application and the range of wavelengths of interest.

Still referencing FIG. 1, as electromagnetic radiation 20 enters defect ridden semiconductor layer 16, layer 16 acts as a waveguide, attenuating electromagnetic radiation 20 as it passes through it, resulting in the output of optically-interacted light 22. When an electromagnetic wave is produced across semiconductor layer 16, metal ions diffuse into defect ridden semiconductor layer 16 (the fundamental mechanism is similar to semiconductor doping). The electromagnetic wave may be produced in a variety of ways, such as, for example, a voltage or current applied across semiconductor layer 16. Nevertheless, the number of metal ions from metal layer 18 diffusing into semiconductor layer 16 increases with an increase in the power level of the electromagnetic wave(s), thus resulting in a decrease in electromagnetic radiation passing through layer 16. The amount of electromagnetic radiation 20 passing through the semiconductor layer 16 increases with a decrease in the power level of the electromagnetic wave(s). This phenomena occurs due to scattering and absorption effects caused by the metal ions diffused into semiconductor layer 16. Accordingly, semiconductor layer 16 can also be referred to as "spectrally alterable material."

Figure 2:
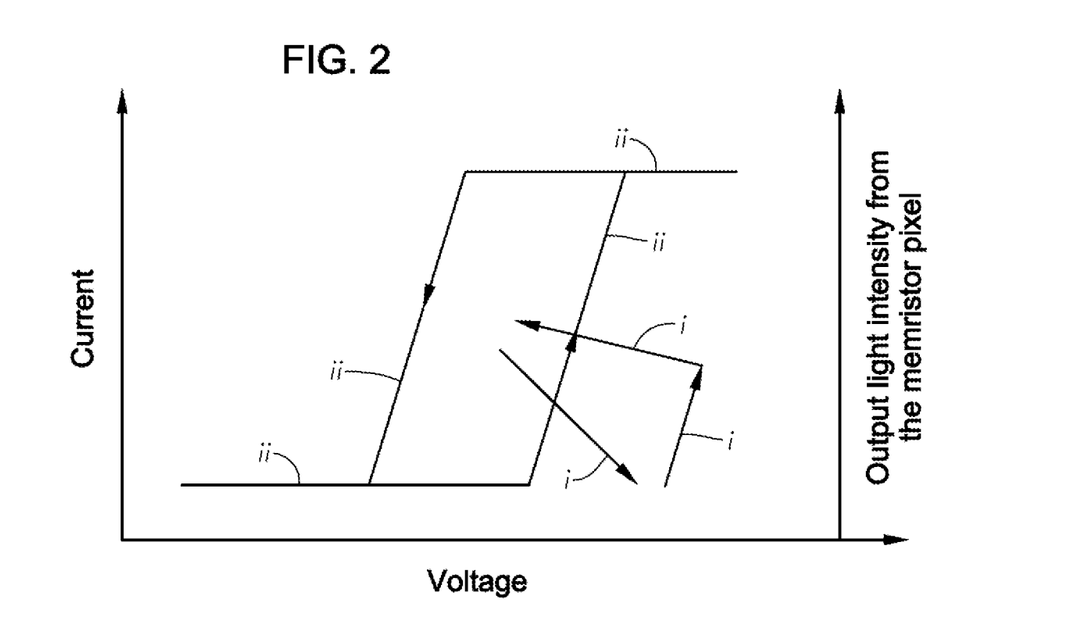
FIG. 2 is a graph which plots the voltage-current hysteresis and output light intensity of a memristor element having one pixel, according to certain illustrative embodiments of the present disclosure.

As previously mentioned, memristor element 100 is comprised of a single pixel, but in other embodiments memristor element 100 may be comprised of a plurality of pixels. FIG. 2 is a graph which plots the voltage-current hysteresis and output light intensity of a memristor element having one pixel, according to certain illustrative embodiments of the present disclosure. The voltage-current hysteresis (ii) of the memristor element is plotted relative to the output light intensity (i). By using the hysteresis curve, the % transmission of electromagnetic radiation through the defect ridden semiconductor layer may be controlled. Such a plot may be used to calibrate the memristor element so that the required amount of electromagnetic energy (e.g., voltage, current, etc.) is applied across each pixel to produce the desired spectral output. Once the voltage/optical transmission relationship across all wavelengths is known for the memristor element, it can be 'programmed' to achieve any transmission/reflection/absorption function.

Still referencing FIG. 1, although not shown, an electromagnetic field producing element is communicably coupled to contacts 14 and metal layer 18 in order to produce the electromagnetic field(s) across semiconductor layer 16. The electromagnetic field producing element may be communicably coupled in a number of ways, such as, for example, via a wired or wireless connection. When wireless methods are utilized, contacts 14 may not be necessary. The electromagnetic field producing element may be a variety of devices, such as, for example, a current source, voltage source, electromagnetic source, magnetic source, thermal source or an ionic source. Regardless of the source used, the result is the diffusion of metal ions into defect ridden semiconductor layer 16 which, in turn, affects the spectral output of memristor element 100.

Figure 3A:
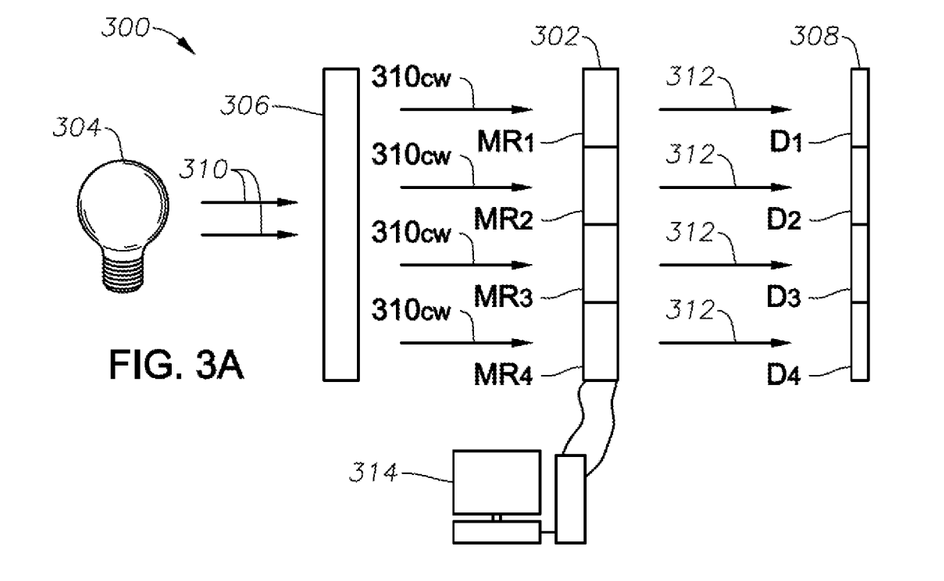
FIG. 3A is a block diagrammatical illustration of a spectrally programmable memristor array in calibration mode, according to certain illustrative embodiments of the present disclosure.

FIG. 3A is a block diagrammatical illustration of a spectrally programmable memristor array in calibration mode, according to certain illustrative embodiments of the present disclosure. Calibration system 300 includes a memristor element 302, which itself is comprised of a memristor array that includes four memristor elements $MR_1$, $MR_2$, $MR_3$ and $MR_4$. Each memristor element $MR_1$ ... $MR_4$ may be made of one or more pixels. Calibration system 300 includes an electromagnetic source 304 (selected based upon the desired application) which produces electromagnetic radiation 310, optical separation device 306, and memristor element array 302 fabricated such that memristor elements $MR_1$ ... $MR_4$ are in parallel with respect to the incoming radiation.

Optical separation device 306 is any device used to separate electromagnetic radiation 310 into component wavelengths, such as, for example, a diffraction grating or spectral splitting element. A diffraction grating uses the principal of diffraction to split light into its component wavelengths, while a spectral splitting element uses refraction (such as prisms, for example) or can use specially designed bandpass filters or notch filters, ring resonators etc.

During operation of calibration system 300, optical separation element 306 splits electromagnetic radiation 310 into its individual component wavelengths $310_{CW}$. Each memristor element $MR_1 \ldots MR_4$ in array 302 is fabricated such that each component wavelength $310_{CW}$ enters at least one memristor element $MR_1 \ldots MR_4$, whereby optically-interacted light 312 is produced. Each memristor element $MR_1 \ldots MR_4$ is designed to correspond to the component wavelength using any variety of techniques. For example, in certain embodiments, the diffraction grating (when used as element 306), memristor array 302 and detector array 308 are aligned such that only one wavelength or a narrow range of wavelengths enters each memristor element $MR_1 \ldots MR_4$ using, for example, nano scale positioners. Alternatively, once the light is split by the diffraction grating, waveguides may also be used to carry the split light into each memristor element $MR_1 \ldots MR_4$. In the illustrated example, optical separation device 306 transmits only one wavelength to each memristor element $MR_1 \ldots MR_4$. In other examples, however, more than one wavelength or a narrow wavelength range may be transmitted.

In order to calibrate memristor array 302 to get the desired transmission/reflection/absorption pattern, optical detector array 308 having detectors $D_1$-$D_4$ is used. In this example, each memristor element $MR_1 \ldots MR_4$ is comprised of a single memristor pixel and, therefore, detector array 308 includes a matching number of detectors. Also during calibration, as shown in FIG. 3A, processing circuitry 314 is coupled to memristor element array 302 in order to program each memristor element $MR_1 \ldots MR_4$. As used herein, calibration is the process performed to find the optical response (output light intensity) of each memristor element. In this process, a range of voltages, for example, are applied to the memristor element, and the output light intensity is measured, as shown in FIG. 2. Once the optical response has been determined, the optical response may then be programmed using, for example, a logic array programmable microchip (represented by processing circuitry 314).

Figure 3B:
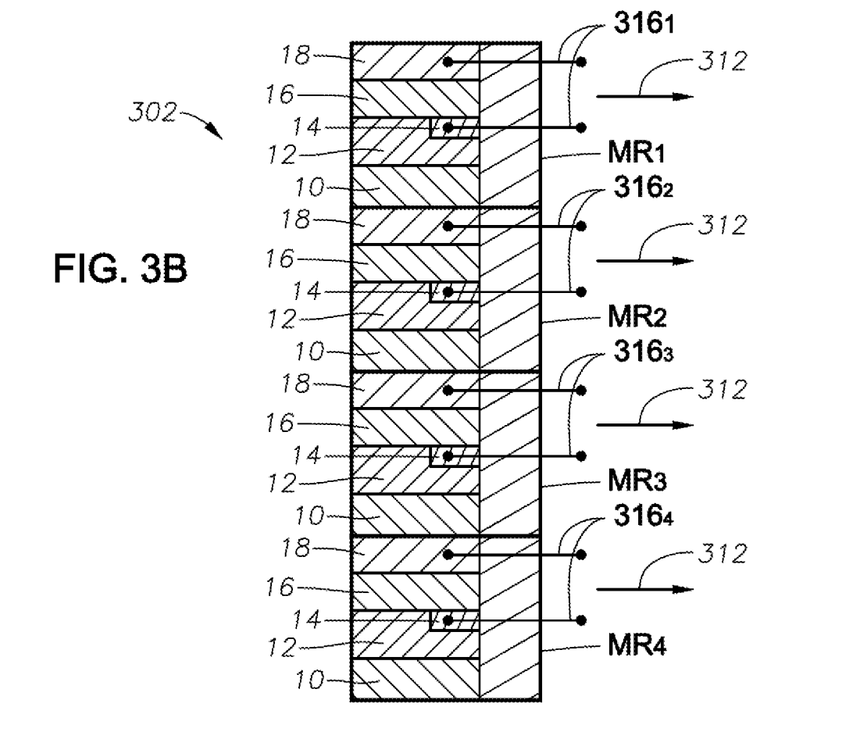
FIG. 3B is an exploded sectional view of the memristor element array of FIG. 3A.

FIG. 3B is an exploded sectional view of memristor element array 302. Unlike memristor element 100 which is arranged in parallel with electromagnetic radiation 20 (such that radiation 20 moves through layer 16 along its axis), memristor element array 302 is arranged in perpendicular to component wavelength $310_{CW}$. Alternatively, there are a variety of ways in which to deposit a memristor element without departing from the scope of this disclosure. Nevertheless, as previously described, contact(s) 14 and metal layer 18 of each memristor element $MR_1 \ldots MR_4$ are communicably coupled to an electromagnetic field producing element (not shown) via leads $316_1$-$316_4$. In other examples, however, the electromagnetic field producing element may be communicably coupled via wireless means. Nevertheless, in this example, wire leads $316_1$-$316_4$ are communicably coupled to a voltage source acting as the electromagnetic field producing element, as well as processing circuitry 314.

Referring to FIG. 3B, in order to perform calibration of memristor array 302, electromagnetic radiation component wavelengths $310_{CW}$ optically interacts with defect ridden semiconductor layer 16. Layer 16 acts as a waveguide, attenuating the light as it passes through it, thereby producing optically-interacted light 312. In this example, a voltage source is used as the electromagnetic field producing element as previously described. Thus, when voltage is applied across defect ridden semiconductor layer 16, metal ions diffuse into layer 16 layer, thereby spectrally altering the semiconductor material in layer 16. The number of metal ions from metal layer 18 diffusing into semiconductor layer 16 increases with an increase in the power level of the electromagnetic wave(s), thus resulting in a decrease in electromagnetic radiation passing through layer 16. The amount of electromagnetic radiation 20 passing through the semiconductor layer 16 increases with a decrease in the power level of the electromagnetic wave(s). The detector (not shown) is used to measure the optical response (output light intensity) coming out of memristor element array 302, which is then utilized to program array 302 using processing circuitry 314.

Again, this phenomena occurs due to scattering and absorption effects caused by the metal ions diffused into semiconductor layer 16. By using the hysteresis curve (e.g., FIG. 2), the % transmission of light through defect ridden semiconductor layer 16 may be controlled. Once the voltage/optical transmission relationship across all wavelengths is known for memristor element array 302, array 302 can be "programmed" to achieve any transmission/reflection/absorption function. Such a method can also be used for any other electromagnetic field producing element used.

Each memristor element $MR_1 \ldots MR_4$ is arranged in an order the desired application requires. For example, this particular example has 4 memristor pixels $MR_1 \ldots MR_4$. However this can be extended to an 'n×n' pixel array. Moreover, the number of pixels in the horizontal and vertical direction can also change with the application.

When memristor element array 302 is utilized in a desired application, each memristor element $MR_1 \ldots MR_4$ may be communicably coupled to its own electromagnetic field producing element via leads 316 or wireless means. In certain illustrative embodiments, each electromagnetic field producing element (coupled to processing circuitry 314) may be programmed to produce electromagnetic fields having differing power levels, thereby providing the ability to alter the semiconductor layer 16 of each memristor element as desired. As a result, each memristor element $MR_1 \ldots MR_4$ may have a different spectral property.

Figure 4:
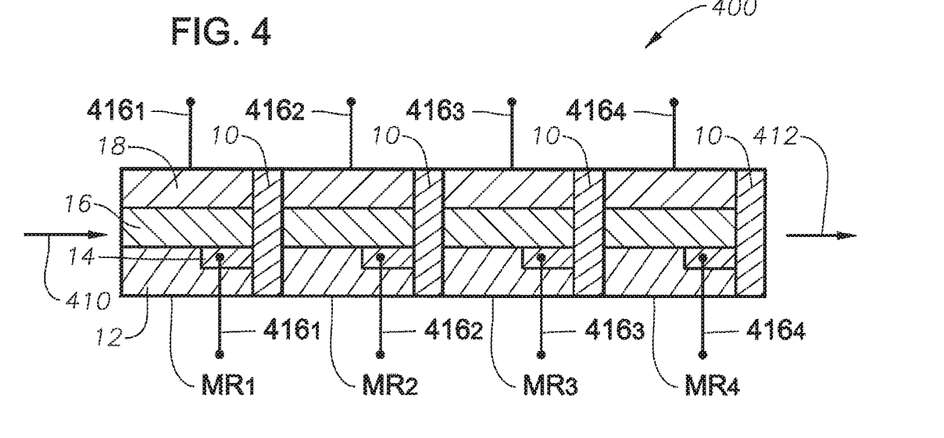
FIG. 4 is a block diagrammatical illustration of a memristor element array for use in an optical computing device, according to an alternative embodiment of the present disclosure.

FIG. 4 is a block diagrammatical illustration of a memristor element array for use in an optical computing device, according to an alternative embodiment of the present disclosure. In this example, memristor element array 400 includes memristor elements $MR_1 \ldots MR_4$ arranged or fabricated in series such that array 400 emulates a traditional thin-film stack consisting of alternating high and low index materials. In this case, each memristor element $MR_1 \ldots MR_4$ is fabricated using a metal layer 18, defect ridden semiconductor layer 16, leads $416_1$-$416_4$, and pure semiconductor layer 12, wherein each memristor element $MR_1 \ldots MR_4$ is separated by a dielectric layer 10. Each memristor element $MR_1 \ldots MR_4$ includes leads $316_1$-$316_4$, as previously described, which communicably coupled to an electromagnetic field producing element (not shown).

In this example, a voltage source is used as the electromagnetic field producing element. As broadband electromagnetic radiation 410 passes through each memristor element $MR_1 \ldots MR_4$ in sequential fashion, radiation 410 optically interacts with each to produce optically-interacted light 412. Thus, when a varied voltage is applied across each memristor element $MR_1 \ldots MR_4$, the ions from metal layer 18 enters defect ridden semiconductor layer 16, effectively decreasing and/or increasing the refractive index of defect ridden semiconductor layers 16. This creates a scenario of a high index material followed by low index material, which is similar to a traditional thin-film design. The number of ions diffusing into defect ridden semiconductor layer 16 is governed by the hysteresis voltage-current curve for the memristor element, as previously described. Moreover, just as in previous embodiments, each memristor element $MR_1 \ldots MR_4$ may be communicably coupled to an electromagnetic field producing element to thereby alter the spectrally alterable material of layer 16.

Now that the fundamental principles of the present disclosure have been provided above, illustrative optical computing devices will now be described. In the most preferred embodiment, the optical computing devices described herein utilize one or more memristor elements to determine characteristics of a sample. As previously described, the memristor element(s) are configured to receive an input of electromagnetic radiation from a substance or sample of the substance and produce an output of electromagnetic radiation that corresponds to a characteristic of the sample. When electromagnetic radiation interacts with a substance, unique physical and chemical information about the substance is encoded in the electromagnetic radiation that is reflected from, transmitted through, or radiated from the sample. Thus, the optical computing device, through use of the memristor element(s), is capable of extracting the information of one or multiple characteristics/properties or analytes within a sample, and converting that information into a detectable output regarding the overall properties of a sample.

The optical computing devices described herein may be utilized in a variety of environments. Such environments may include, for example, downhole well or completion applications. Other environments may include those as diverse as those associated with surface and undersea monitoring, satellite or drone surveillance, pipeline monitoring, or even sensors transiting a body cavity such as a digestive tract. Within those environments, the optical computing devices are utilized to detect/monitor sample characteristics in real time.

Figure 5:
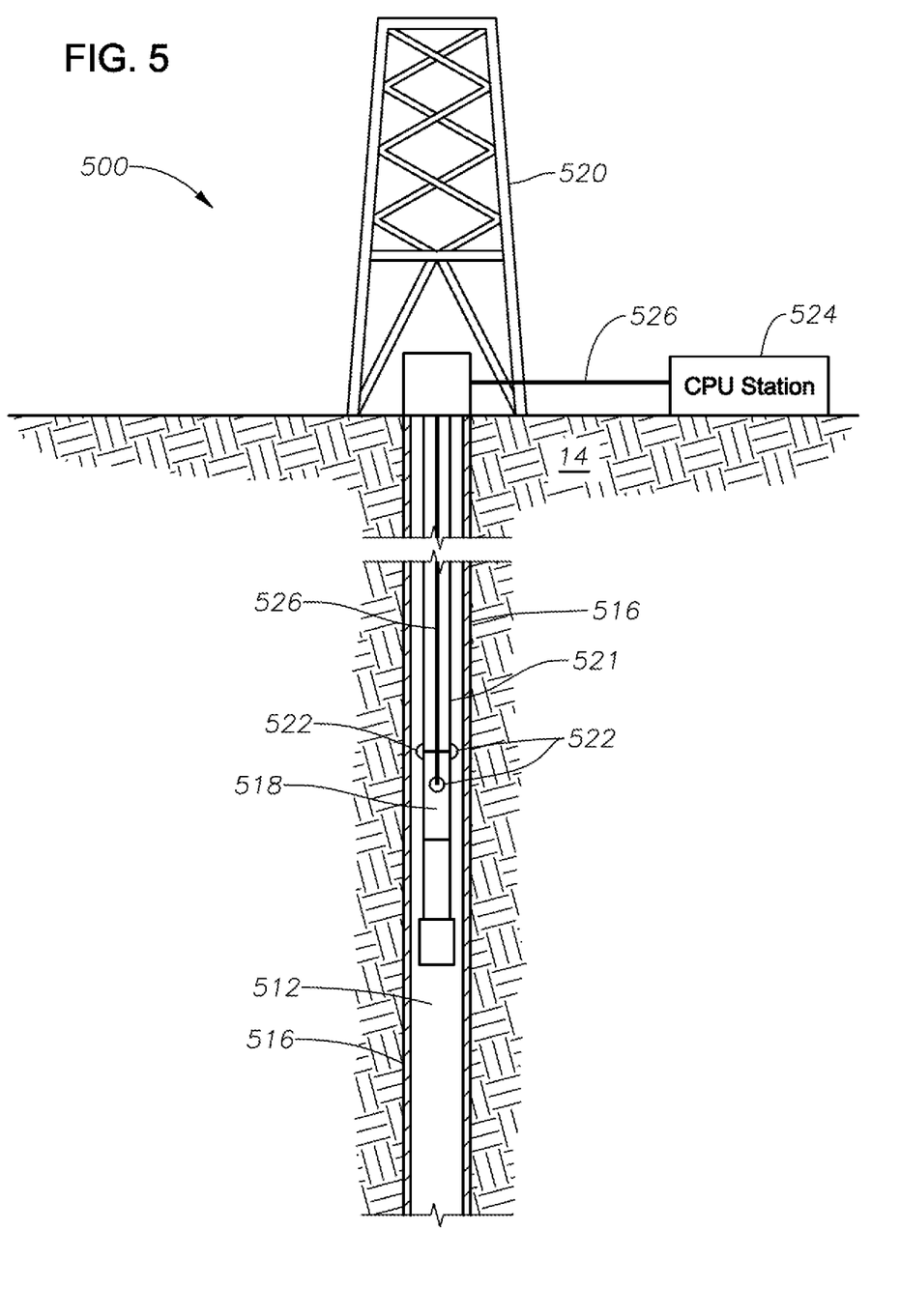
FIG. 5 illustrates a plurality of spectrally programmable optical computing devices positioned along a workstring extending along a downhole well system 500 according to certain illustrative embodiments of the present disclosure.

Although the optical computing devices described herein may be utilized in a variety of environments, the following description will focus on downhole well applications. FIG. 5 illustrates a plurality of spectrally programmable optical computing devices 522 positioned along a workstring 521 extending along a downhole well system 500 according to certain illustrative embodiments of the present disclosure. Workstring 521 may be, for example, a logging assembly, production string or drilling assembly (e.g., logging-while drilling ("LWD"), measurement-while drilling ("MWD"), etc.). Alternatively, optical computing devices 522 may also be deployed in a wireline application. Nevertheless, well system 500 comprises a vertical wellbore 512 extending down into a hydrocarbon formation 514 (although not illustrated, wellbore 512 may also comprise one or more lateral sections). Wellbore equipment 520 is positioned atop vertical wellbore 512, as understood in the art. Wellbore equipment may be, for example, a blow out preventer, derrick, floating platform, etc. As understood in the art, after vertical wellbore 512 is formed, tubulars 516 (casing, for example) are extended therein to complete wellbore 512.

One or more spectrally programmable optical computing devices 522 may be positioned along wellbore 512 at any desired location. In certain embodiments, optical computing devices 522 are positioned along the internal or external surfaces of downhole tool 518 (as shown in FIG. 5) which may be, for example, intervention equipment, surveying equipment, or completion equipment including valves, packers, screens, mandrels, gauge mandrels, in addition to casing or tubing tubulars/joints. Alternatively, however, optical computing devices 522 may be permanently or removably attached to tubulars 516 and distributed throughout wellbore 512 in any area in which sample evaluation is desired. Optical computing devices 522 may be coupled to a remote power supply (located on the surface or a power generator positioned downhole along the wellbore, for example), while in other embodiments each optical computing device 522 comprises an on-board battery. Moreover, optical computing devices 522 are communicably coupled to a CPU station 524 via a communications link 26, such as, for example, a wireline, inductive coupling or other suitable communications link. The number and location of optical computing devices 522 may be manipulated as desired.

Each optical computing device 522 comprises one or more memristor elements which optically interact with a sample of interest (wellbore fluid, downhole tool component, tubular, formation, for example) to determine a sample characteristic. In certain illustrative embodiments, optical computing devices 522 may be dedicated to sample characteristic detection, as well as formation evaluation. Optical computing devices 522 may also determine the presence and quantity of specific inorganic gases such as, for example, $CO_2$ and $H_2S$, organic gases such as methane (C1), ethane (C2) and propane (C3) and saline water, in addition to dissolved ions (Ba, Cl, Na, Fe, or Sr, for example) or various other characteristics (p.H., density and specific gravity, viscosity, total dissolved solids, sand content, etc.). Furthermore, the presence of formation characteristic data (porosity, formation chemical composition, etc.) may also be determined. In certain embodiments, a single optical computing device 522 may detect a single characteristic, while in others a single optical computing device 522 may determine multiple characteristics.

CPU station 524 comprises a signal processor (not shown), communications module (not shown) and other circuitry necessary to achieve the objectives of the present disclosure. In addition, it will also be recognized that the software instructions necessary to carry out the objectives of the present disclosure may be stored within storage located in CPU station 524 or loaded into that storage from a CD-ROM or other appropriate storage media via wired or wireless methods. Communications link 526 provides a medium of communication between CPU station 524 and optical computing devices 522. Communications link 526 may be a wired link, such as, for example, a wireline or fiber optic cable extending down into vertical wellbore 512. Alternatively, however, communications link 526 may be a wireless link, such as, for example, an electromagnetic device of suitable frequency, or other methods including acoustic communication and like devices.

In certain illustrative embodiments, CPU station 524, via its signal processor, controls operation of each optical computing device 522. In addition to sensing operations, CPU station 524 may also control activation and deactivation of optical computing devices 522. Optical computing devices 522 each include a transmitter and receiver (transceiver, for example) (not shown) that allows bi-directional communication over communications link 526 in real-time. In certain illustrative embodiments, optical computing devices 522 will transmit all or a portion of the sample characteristic data to CPU station 524 for further analysis. However, in other embodiments, such analysis is completely handled by each optical computing device 522 and the resulting data is then transmitted to CPU station 524 for storage or subsequent analysis. In either embodiment, the processor handling the computations analyzes the characteristic data and, through utilization of Equation of State ("EOS"), other optical analysis techniques, derives the sample characteristic indicated by the transmitted data.

Still referring to the illustrative embodiment of FIG. 5, optical computing devices 522 are positioned along workstring 521 at any desired location. In this example, optical computing devices 522 are positioned along the outer diameter of downhole tool 518. Optical computing devices 522 have a temperature and pressure resistant housing sufficient to withstand the harsh downhole environment. A variety of materials may be utilized for the housing, including, for example, stainless steels and their alloys, titanium and other high strength metals, and even carbon fiber composites and sapphire or diamond structures, as understood in the art. In certain embodiments, optical computing devices 522 are dome-shaped modules (akin to a vehicle dome light) which may be permanently or removably attached to a surface using a suitable method (welding, magnets, etc.). Module housing shapes may vary widely, provided they isolate components from the harsh down-hole environment while still allowing a unidirectional or bidirectional optical (or electromagnetic radiation) pathway from sensor to the sample of interest. Dimensions would be determined by the specific application and environmental conditions.

Alternatively, optical computing devices 522 may form part of downhole tool 518 (as shown in FIG. 5) along its inner diameter (to detect the presence of fluids flowing through tool 518, for example) or outer diameter (to detect presence of fluids flowing through the annulus between workstring 521 and tubulars 516 or formation characteristic data, for example). In other embodiments as will be described below, optical computing devices 522 may be coupled to downhole tool 518 using an extendable arm (adjustable stabilizer, casing scraper, downhole tractor, for example) in order to extend optical computing device 522 into close proximity with another surface (casing, tool body, formation, etc.) to thereby detect sample characteristics. As previously described, optical computing devices 522 may also be permanently affixed to the inner diameter of tubular 516 by a welding or other suitable process. However, in yet another embodiment, optical computing devices 522 are removably affixed to the inner diameter of tubulars 516 using magnets or physical structures so that optical computing devices 522 may be periodically removed for service purposes or otherwise.

Figure 6:
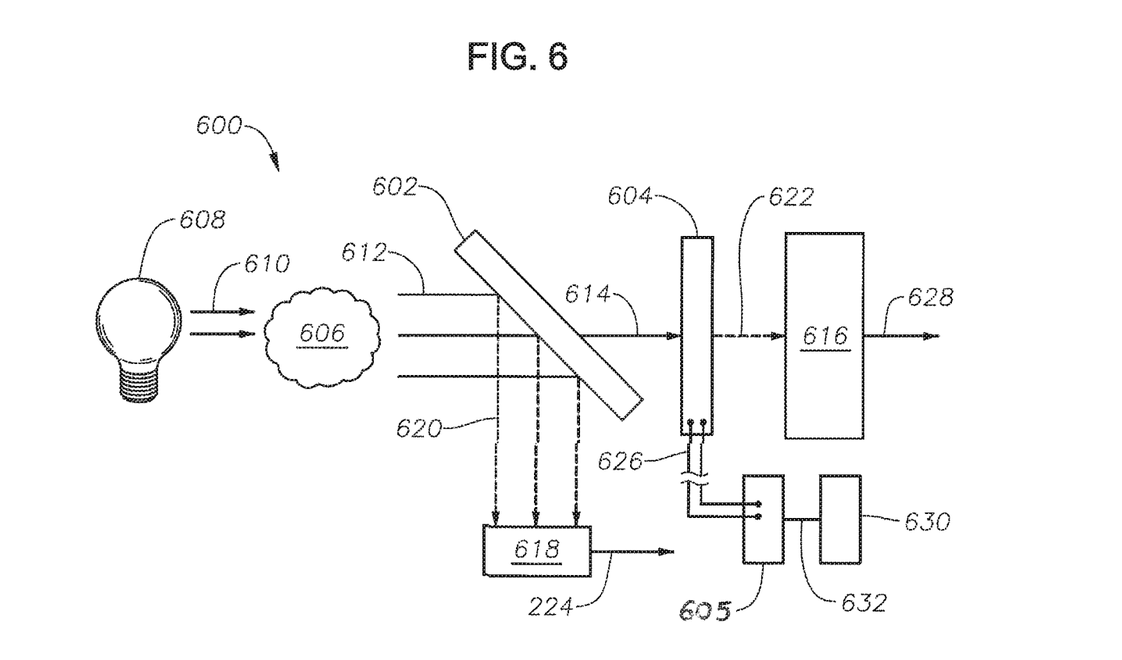
FIG. 6 is a block diagram of a spectrally programmable optical computing device employing a transmission mode design, according to certain illustrative embodiments of the present disclosure.

FIG. 6 is a block diagram of a spectrally programmable optical computing device 600 employing a transmission mode design, according to certain illustrative embodiments of the present disclosure. An electromagnetic radiation source 608 may be configured to emit or otherwise generate electromagnetic radiation 610. As understood in the art, electromagnetic radiation source 608 may be any device capable of emitting or generating electromagnetic radiation. For example, electromagnetic radiation source 608 may be a light bulb, light emitting device, laser, blackbody, photonic crystal, or X-Ray source, etc. In one embodiment, electromagnetic radiation 610 may be configured to optically interact with the sample 606 (wellbore fluid flowing through wellbore 512 or a portion of the formation 514, for example) and generate sample-interacted light 612 directed to a beam splitter 602. Sample 606 may be any fluid (liquid or gas), solid substance or material such as, for example, downhole tool components, tubulars, rock formations, slurries, sands, muds, drill cuttings, concrete, other solid surfaces, etc. In other embodiments, however, sample 606 is a multiphase wellbore fluid (comprising oil, gas, water, solids, for example) consisting of a variety of fluid characteristics such as, for example, C1-C4 and higher hydrocarbons, groupings of such elements, and saline water. However, if the sample where a downhole tool component, the characteristic data may correspond to physical defects in the surface of the component such as, for example, pitting.

Sample 606 may be provided to optical computing device 600 through a flow pipe or sample cell, for example, containing sample 606, whereby it is introduced to electromagnetic radiation 610. Alternatively, optical computing device 600 may utilize an optical configuration consisting of an internal reflectance element which analyzes the wellbore fluid as it flows thereby or which analyzes the surface of the sample (formation surface, for example). While FIG. 6 shows electromagnetic radiation 610 as passing through or incident upon the sample 606 to produce sample-interacted light 612 (i.e., transmission or fluorescent mode), it is also contemplated herein to reflect electromagnetic radiation 610 off of the sample 606 (i.e., reflectance mode), such as in the case of a sample 606 that is translucent, opaque, or solid, and equally generate the sample-interacted light 612.

After being illuminated with electromagnetic radiation 610, sample 606 containing an analyte of interest (a characteristic of the sample, for example) produces an output of electromagnetic radiation (sample-interacted light 612, for example). Ultimately, CPU station 524 (or a processor on-board device 600) analyzes this spectral information to determine one or more sample characteristics. Although not specifically shown, one or more spectral elements may be employed in optical computing device 600 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Still referring to the illustrative embodiment of FIG. 6, beam splitter 602 is employed to split sample-interacted light 612 into a transmitted electromagnetic radiation 614 and a reflected electromagnetic radiation 620. Transmitted electromagnetic radiation 614 is then directed to memristor element 604. Memristor element 604 may be any of the memristor elements described herein, in which the memristor element has been configured to be associated with a particular characteristic of sample 606 or may be designed to approximate or mimic the regression vector of the characteristic in a desired manner.

Memristor element 604 is communicably coupled to an electromagnetic field producing element 605 via a wire leads 626. Although shown as a single electromagnetic field producing element, it may be comprised of multiple electromagnetic field producing elements when memristor element 604 includes a plurality of pixels or is an array. In such embodiments, each memristor element in the array may have its own dedicated wire leads or other suitable coupling mechanism. Alternatively, electromagnetic field producing element 605 may be communicably coupled to memristor element 604 via wireless means. Electromagnetic field producing element 605 may be a variety of devices, such as, for example, a current source, voltage source, electromagnetic source, magnetic source, thermal source or an ionic source. For example, electromagnetic field producing element 605 may be an electromagnetic field source which generates an electromagnetic wave and emits it toward memristor element 604. The electromagnetic wave will in turn induce a current across memristor element 604 which will alter the spectral properties the defect ridden semiconductor layer, as described herein.

Still referring to FIG. 6, spectrally programmable optical computing device 600 also includes a power management module 630 communicably coupled to electromagnetic field producing element 605 via connection 632 to thereby control the power output of electromagnetic field producing element 605 to memristor element 604. In certain illustrative embodiments, power management module 630 is a pre-programmed power management chip which controls the voltage across each memristor element (when a memristor array is used) to thereby achieve the desired transmission function(s). In such embodiments, power management module includes processing circuitry which controls the operation of electromagnetic field producing element 605 to thereby supply the required voltage (or other electromagnetism) to each memristor element to affect the output function. Power management module may be included in CPU station 524 or may be its own stand-alone module on-board device 600.

Once the spectral output of memristor element 604 has been programmed by power management module 600, transmitted electromagnetic radiation 614 optically interacts with memristor element 604 to produce optically interacted light 622. In this embodiment, optically interacted light 622, which is related to the characteristic or analyte of interest, is conveyed to detector 616 for analysis and quantification. Detector 616 may be any device capable of detecting electromagnetic radiation, and may be generally characterized as an optical transducer. For example, detector 616 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, any such arrays, and/or combinations thereof, or the like, or other detectors known to those ordinarily skilled in the art. Detector 616 is further configured to produce an output signal 628 in the form of a voltage that corresponds to the characteristic of the sample 606. In at least one embodiment, output signal 628 produced by detector 616 and the characteristic concentration of the sample 606 may be directly proportional. In other embodiments, the relationship may be a polynomial function, an exponential function, and/or a logarithmic function.

Optical computing device 600 includes a second detector 618 arranged to receive and detect reflected electromagnetic radiation and output a normalizing signal 624. As understood in the art, reflected electromagnetic radiation 620 may include a variety of radiating deviations stemming from electromagnetic radiation source 608 such as, for example, intensity fluctuations in the electromagnetic radiation, interferent fluctuations (for example, dust or other interferents passing in front of the electromagnetic radiation source), combinations thereof, or the like. Thus, second detector 618 detects such radiating deviations as well. In an alternative embodiment, second detector 618 may be arranged to receive a portion of the sample-interacted light 612 instead of reflected electromagnetic radiation 620, and thereby compensate for electromagnetic radiating deviations stemming from the electromagnetic radiation source 608. In yet other embodiments, second detector 618 may be arranged to receive a portion of electromagnetic radiation 610 instead of reflected electromagnetic radiation 620, and thereby likewise compensate for electromagnetic radiating deviations stemming from the electromagnetic radiation source 608. Any variety of design alterations which may be utilized in conjunction with the present disclosure.

Although not shown in FIG. 6, in certain illustrative embodiments, detector 616 and second detector 618 may be communicably coupled to power management module 630 or another signal processor on-board optical computing device 200 such that normalizing signal 624 indicative of electromagnetic radiating deviations may be provided or otherwise conveyed thereto. The signal processor may then be configured to computationally combine normalizing signal 624 with output signal 628 to provide a more accurate determination of the characteristic of sample 606. However, in other embodiments that utilized only one detector, the signal processor would be coupled to the one detector. Nevertheless, in the embodiment of FIG. 6, for example, the signal processor computationally combines normalizing signal 624 with output signal 628 via principal component analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®). Thereafter, the resulting data is then transmitted to CPU station 524 via communications link 526 for further operations.

Those ordinarily skilled in the art having the benefit of this disclosure realize the aforementioned optical computing device is illustrative in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams. The multiple beams may then simultaneously go through corresponding memristor elements, whereby multiple characteristics and/or analytes of interest are simultaneously detected.

The parallel processing configuration is particularly useful in those applications that require extremely low power or no moving parts. In yet another alternate embodiment, various memristor elements may be positioned in series in a single optical computing device. This embodiment is particularly useful if it is necessary to measure the concentrations of the analytes in different locations (in each individual mixing pipe, for example). It is also sometimes helpful if each of the memristor elements use two substantially different light sources (UV and IR, for example) to cover the optical activity of all the characteristics or analytes of interest (i.e., some analytes might be only UV active, while others are IR active). Nevertheless, the choice of a specific optical configuration is mainly dependent upon the specific application and analytes of interest.

Moreover, the memristor elements utilized in certain embodiments of the present disclosure may not be semiconductor-based. For example, plastic-based memristor elements or grapheme-based elements may also be utilized.

Embodiments described herein further relate to any one or more of the following paragraphs:

1. A spectrally programmable optical computing device, comprising: electromagnetic radiation that optically interacts with a sample to produce sample-interacted light; a memristor element comprising spectrally alterable material, the memristor element being positioned to optically interact with the sample-interacted light to produce optically-interacted light which corresponds to a characteristic of the sample; an electromagnetic field produced across the memristor element to alter the spectrally alterable material, thereby altering a spectral property of the electromagnetic radiation to produce the optically-interacted light; and a detector positioned to measure the optically-interacted light and generate a signal, wherein the signal is utilized to determine the characteristic of the sample.

2. An optical computing device as defined in paragraph 1, further comprising an electromagnetic field producing element communicably coupled to the memristor element to produce the electromagnetic field across the memristor element.

3. An optical computing device as defined in paragraphs 1 or 2, wherein the electromagnetic field producing element is a current source, voltage source, electromagnetic source, magnetic source, thermal source or ionic source.

4. An optical computing device as defined in any of paragraphs 1-3, further comprising a power management module communicably coupled to the electromagnetic field producing element to thereby produce different power levels.

5. An optical computing device as defined in any of paragraphs 1-4, wherein the memristor element comprises one or more memristor pixels.

6. An optical computing device as defined in any of paragraphs 1-5, wherein the memristor element is a memristor element array comprising a plurality of memristor elements.

7. An optical computing device as defined in any of paragraphs 1-6, wherein each memristor element is communicably coupled to an electromagnetic field producing element to thereby produce the electromagnetic field across each memristor element.

8. An optical computing device as defined in any of paragraphs 1-7, whereby each memristor element comprises a different spectral property produced by the electromagnetic field applied there across.

9. An optical computing device as defined in any of paragraphs 1-8, further comprising: an electromagnetic radiation source to generate the electromagnetic radiation; and an optical separation element positioned to separate the electromagnetic radiation into component wavelengths and to direct the component wavelengths to a corresponding memristor element.

10. An optical computing device as defined in any of paragraphs 1-9, wherein the optical separation element is a diffraction element or spectral splitting element.

11. An optical computing device as defined in any of paragraphs 1-10, wherein each memristor element in the memristor array corresponds to a different component wavelength of the electromagnetic radiation.

12. An optical computing device as defined in any of paragraphs 1-11, wherein the memristor element is a memristor element array comprising a plurality of memristor elements positioned to optically interact with the electromagnetic radiation in a sequential fashion.

13. An optical computing device as defined in any of paragraphs 1-12, wherein each memristor element is communicably coupled to an electromagnetic field producing element to thereby produce the electromagnetic field across each memristor element of the memristor element array.

14. An optical computing device as defined in any of paragraphs 1-13, whereby each memristor element of the memristor element array comprises a different spectral property produced by the electromagnetic field.

15. An optical computing device as defined in any of paragraphs 1-14, further comprising a signal processor communicably coupled to the detector to computationally determine the characteristic of the sample.

16. An optical computing device as defined in any of paragraphs 1-15, wherein the optical device comprises part of a reservoir interrogation device.

17. An optical computing method, comprising: optically interacting electromagnetic radiation with a sample to produce sample-interacted light; applying an electromagnetic field across a memristor element having spectrally alterable material, thereby altering the spectrally alterable material; optically interacting the sample-interacted light with the memristor element to produce optically-interacted light which corresponds to a characteristic of the sample; detecting the optically-interacted light and thereby generating a signal which corresponds to the optically-interacted light; and determining the characteristic of the sample using the signal.

18. An optical computing method as defined in paragraph 17, wherein an electromagnetic field producing element is utilized to generate the electromagnetic field applied across the memristor element.

19. An optical computing method as defined in paragraphs 17 or 18, wherein the electromagnetic field producing element is a current source, voltage source, electromagnetic source magnetic source, thermal source or ionic source.

20. An optical computing method as defined in any of paragraphs 17-19, further comprising utilizing a power management module to produce differing power levels of electromagnetic fields.

21. An optical computing method as defined in any of paragraphs 17-20, wherein: the memristor element is a memristor element array comprising a plurality of memristor elements, each memristor element being communicably coupled to an electromagnetic field producing element; and the method further comprises using the electromagnetic field producing elements to produce an electromagnetic field across each memristor element.

22. An optical computing method as defined in any of paragraphs 17-21, further comprising altering a spectral property of each memristor element such that each spectral property is different.

23. An optical computing method as defined in any of paragraphs 17-22, further comprising: separating the electromagnetic radiation into component wavelengths; and directing the component wavelengths to a corresponding memristor element.

24. An optical computing method as defined in any of paragraphs 17-23, wherein the memristor element is memristor element array comprising a plurality of memristor elements; and the method further comprises optically interacting the electromagnetic radiation with the memristor elements in sequential fashion.

25. An optical computing method as defined in any of paragraphs 17-24, wherein: each memristor element is communicably coupled to an electromagnetic field producing element; and the method further comprises using the electromagnetic field producing elements to produce electromagnetic fields across each memristor element.

26. An optical computing method as defined in any of paragraphs 17-25, further comprising using the electromagnetic fields to produce a different spectral property in each memristor element.

27. An optical computing method as defined in any of paragraphs 17-26, further comprising utilizing the optical computing method to interrogate a downhole reservoir.

28. An optical computing method, comprising: optically interacting electromagnetic radiation with a sample to produce sample-interacted light; optically interacting the sample-interacted light with a memristor element to produce optically-interacted light which corresponds to a characteristic of the sample; and determining the characteristic of the sample using the optically-interacted light.

29. An optical computing method as defined in paragraph 28, wherein: the memristor element comprises spectrally alterable material; and the method further comprises altering the spectrally alterable material, thereby altering a spectral property of the optically-interacted light.

30. An optical computing method as defined in paragraphs 28 or 29, wherein an electromagnetic field is produced across the memristor element in order to alter the spectrally alterable material.

31. An optical computing method as defined in any of paragraphs 28-30, wherein differing power levels of the electromagnetic field are produced across the memristor element.

32. An optical computing method as defined in any of paragraphs 28-31, further comprising using the optical computing method to interrogate a downhole reservoir.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A spectrally programmable optical computing device, comprising:
    electromagnetic radiation that optically interacts with a sample to produce a sample-interacted light;
    a memristor element comprising a spectrally alterable material, the memristor element being positioned to optically interact with the sample-interacted light to produce optically-interacted light which corresponds to a characteristic of the sample;
    an electromagnetic field produced across the memristor element to alter the spectrally alterable material, thereby altering a spectral property of the electromagnetic radiation to produce the optically-interacted light; and
    a detector positioned to measure the optically-interacted light and generate a signal,
    wherein the signal is utilized to determine the characteristic of the sample.

2. An optical computing device as defined in claim 1, further comprising an electromagnetic field producing element communicably coupled to the memristor element to produce the electromagnetic field across the memristor element.

3. An optical computing device as defined in claim 2, further comprising a power management module communicably coupled to the electromagnetic field producing element to thereby produce different power levels.

4. An optical computing device as defined in claim 1, wherein the memristor element is a memristor element array comprising a plurality of memristor elements.

5. An optical computing device as defined in claim 4, wherein each memristor element is communicably coupled to an electromagnetic field producing element to thereby produce the electromagnetic field across each memristor element.

6. An optical computing device as defined in claim 5, whereby each memristor element comprises a different spectral property produced by the electromagnetic field applied there across.

7. An optical computing device as defined in claim 4, further comprising:
    an electromagnetic radiation source to generate the electromagnetic radiation; and
    an optical separation element positioned to separate the electromagnetic radiation into component wavelengths and to direct the component wavelengths to a corresponding memristor element.

8. An optical computing device as defined in claim 1, wherein the memristor element is a memristor element array comprising a plurality of memristor elements positioned to optically interact with the electromagnetic radiation in a sequential fashion.

9. An optical computing device as defined in claim 8, wherein each memristor element is communicably coupled to an electromagnetic field producing element to thereby produce the electromagnetic field across each memristor element of the memristor element array.

10. An optical computing device as defined in claim 1, further comprising a signal processor communicably coupled to the detector to computationally determine the characteristic of the sample.

11. An optical computing device as defined in claim 1, wherein the optical device comprises part of a reservoir interrogation device.

12. An optical computing method, comprising:
    optically interacting electromagnetic radiation with a sample to produce a sample-interacted light;
    applying an electromagnetic field across a memristor element having a spectrally alterable material, thereby altering the spectrally alterable material;
    optically interacting the sample-interacted light with the memristor element to produce optically-interacted light which corresponds to a characteristic of the sample;
    detecting the optically-interacted light and thereby generating a signal which corresponds to the optically-interacted light; and
    determining the characteristic of the sample using the signal.

13. An optical computing method as defined in claim 12, wherein an electromagnetic field producing element is utilized to generate the electromagnetic field applied across the memristor element.

14. An optical computing method as defined in claim 13, further comprising utilizing a power management module to produce differing power levels of electromagnetic fields.

15. An optical computing method as defined in claim 12, wherein:
    the memristor element is a memristor element array comprising a plurality of memristor elements, each memristor element being communicably coupled to an electromagnetic field producing element; and
    the method further comprises using the electromagnetic field producing elements to produce an electromagnetic field across each memristor element.

16. An optical computing method as defined in claim 15, further comprising altering a spectral property of each memristor element such that each spectral property is different.

17. An optical computing method as defined in claim 15, further comprising:
    separating the electromagnetic radiation into component wavelengths; and
    directing the component wavelengths to a corresponding memristor element.

18. An optical computing method as defined in claim 12, wherein:
    the memristor element is a memristor element array comprising a plurality of memristor elements; and the method further comprises optically interacting the electromagnetic radiation with the memristor elements in sequential fashion.

19. An optical computing method as defined in claim 18, wherein:
each memristor element is communicably coupled to an electromagnetic field producing element; and
the method further comprises using the electromagnetic field producing elements to produce electromagnetic fields across each memristor element to thereby produce a different spectral property in each memristor element.

20. An optical computing method as defined in claim 12, further comprising utilizing the optical computing method to interrogate a downhole reservoir.

21. An optical computing method, comprising:
optically interacting electromagnetic radiation with a sample to produce a sample-interacted light;
optically interacting the sample-interacted light with a memristor element to produce optically-interacted light which corresponds to a characteristic of the sample; and
determining the characteristic of the sample using the optically-interacted light.

22. An optical computing method as defined in claim 21, wherein:
the memristor element comprises a spectrally alterable material; and
the method further comprises altering the spectrally alterable material, thereby altering a spectral property of the optically-interacted light.

23. An optical computing method as defined in claim 22, wherein an electromagnetic field is produced across the memristor element in order to alter the spectrally alterable material.

24. An optical computing method as defined in claim 23, wherein differing power levels of the electromagnetic field are produced across the memristor element.

25. An optical computing method as defined in claim 21, further comprising using the optical computing method to interrogate a downhole reservoir.

* * * * *